US012623980B2

(12) United States Patent  (10) Patent No.: US 12,623,980 B2
Ghosh et al.  (45) Date of Patent: May 12, 2026

(54) SEPARATION OF HYDROGEN, METHANE, ETHANE, AND PROPANE IN NAPHTHA TO ETHANE AND PROPANE FRACTIONATION SECTION BASED ON A DIVIDING WALL FRACTIONATION COLUMN INTEGRATION

(71) Applicant: UOP LLC, Des Plaines, IL (US)

(72) Inventors: Sudipta K. Ghosh, Haryana (IN); Xin X. Zhu, Des Plaines, IL (US); Kyle Cuellar, Fulshear, TX (US)

(73) Assignee: UOP LLC, Des Plaines, IL (US)

( * ) Notice: Subject to any disclaimer, the term of this patent is extended or adjusted under 35 U.S.C. 154(b) by 181 days.

(21) Appl. No.: 18/508,452

(22) Filed: Nov. 14, 2023

(65) Prior Publication Data

US 2024/0190791 A1     Jun. 13, 2024

Related U.S. Application Data

(60) Provisional application No. 63/431,557, filed on Dec. 9, 2022.

(51) Int. Cl.
| | |
|---|---|
| *C07C 4/04* | (2006.01) |
| *B01J 12/00* | (2006.01) |
| *B01J 19/00* | (2006.01) |
| *B01J 19/24* | (2006.01) |
| *C07C 5/327* | (2006.01) |
| *C07C 5/333* | (2006.01) |
| *F25J 3/02* | (2006.01) |

(52) U.S. Cl.
CPC ................. *C07C 4/04* (2013.01); *B01J 12/00* (2013.01); *B01J 19/0013* (2013.01); *B01J 19/245* (2013.01); *C07C 5/333* (2013.01); *F25J 3/0219* (2013.01); *F25J 3/0238*

(2013.01); *F25J 3/0295* (2013.01); *B01J 2219/00103* (2013.01); *F25J 2215/62* (2013.01); *F25J 2215/64* (2013.01)

(58) Field of Classification Search
CPC .......... C07C 4/04; C07C 5/327; B01J 19/245; B01J 2219/00006; B01D 3/141; F25J 3/0238; F25J 3/0295; F25J 2215/62; F25J 2215/64
See application file for complete search history.

(56) References Cited

U.S. PATENT DOCUMENTS

| | | | |
|---|---|---|---|
| 2006/0135840 A1* | 6/2006 | Reyneke ................ | F25J 3/0242 585/809 |
| 2008/0081937 A1* | 4/2008 | Schultz .................... | C10G 7/02 585/648 |
| 2010/0145120 A1 | 6/2010 | Bouvart et al. | |
| 2016/0369186 A1 | 12/2016 | Dittrich et al. | |
| 2021/0189257 A1* | 6/2021 | Singh ...................... | B01J 8/1827 |
| 2021/0363438 A1* | 11/2021 | Al-Shafei .............. | C10G 51/04 |
| 2024/0190792 A1* | 6/2024 | Ghosh .................... | B01D 3/143 |

FOREIGN PATENT DOCUMENTS

WO      2014067955 A1      5/2014

OTHER PUBLICATIONS

International Search Report from corresponding PCT application No. PCT/US2023/082326, mailed Apr. 16, 2024.
Written Opinion from corresponding PCT application No. PCT/US2023/082326, mailed Apr. 16, 2024.

* cited by examiner

*Primary Examiner* — Randy Boyer

(57) ABSTRACT

In a process of producing ethylene and propylene from naphtha the process a feed stream comprising hydrogen, methane, ethane, and propane and residual C4+ from a naphtha-to-ethane-and-propane reactor is fed to a dividing wall fractionation column.

12 Claims, 5 Drawing Sheets

SEPARATION OF HYDROGEN, METHANE, ETHANE, AND PROPANE IN NAPHTHA TO ETHANE AND PROPANE FRACTIONATION SECTION BASED ON A DIVIDING WALL FRACTIONATION COLUMN INTEGRATION

RELATED APPLICATIONS

This application claims the benefit of and priority to U.S. Provisional Patent Application No. 63/431,557 filed on Dec. 9, 2022, the entirety of which is incorporated herein by reference.

TECHNICAL FIELD

This invention relates generally to separating ethane and propane from an effluent stream, containing ethane, propane and also hydrogen, methane, and some C4+ material, of a naphtha to ethane and propane reactor section. More particularly, the invention relates to separating ethane and propane from the effluent using a dividing wall fractionation column.

BACKGROUND

Naphtha fed to a naphtha cracker produces olefins, namely ethylene and propylene. There is an industry trend towards shifting refining capacity to make increased petrochemicals due to the high value and market demand of ethylene and propylene compared to fuels. Naphtha steam cracking is the industry standard for making ethylene and propylene from naphtha, but ethylene plus propylene yields are low—less than 60% and typically less than 50% by weight depending on naphtha composition.

The present invention is provided to solve the problems discussed above and other problems, and to provide advantages and aspects not provided by prior process and apparatuses of this type. A full discussion of the features and advantages of the present invention is deferred to the following detailed description, which proceeds with reference to the accompanying drawings.

SUMMARY

The disclosure is directed to a process of producing light paraffins from naphtha from a stream comprising hydrogen, methane, ethane, propane and C4+ produced in a reactor section of a naphtha-to-ethane-and-propane (NEP) processing unit. The process includes passing a NEP reactor effluent stream comprising hydrogen, methane, ethane, and propane and residual C4+ to the NEP fractionation section for efficiently separating the effluent stream into components. The NEP fractionation section comprises, among other equipment, coldbox (cryogenic) exchangers, and dividing wall fractionation column.

Other features and advantages of the invention will be apparent from the following specification taken in conjunction with the following drawings.

BRIEF DESCRIPTION OF THE DRAWINGS

One or more exemplary embodiments of the present invention will be described below in conjunction with the following drawing figures, in which.

DETAILED DESCRIPTION

Figure 1:
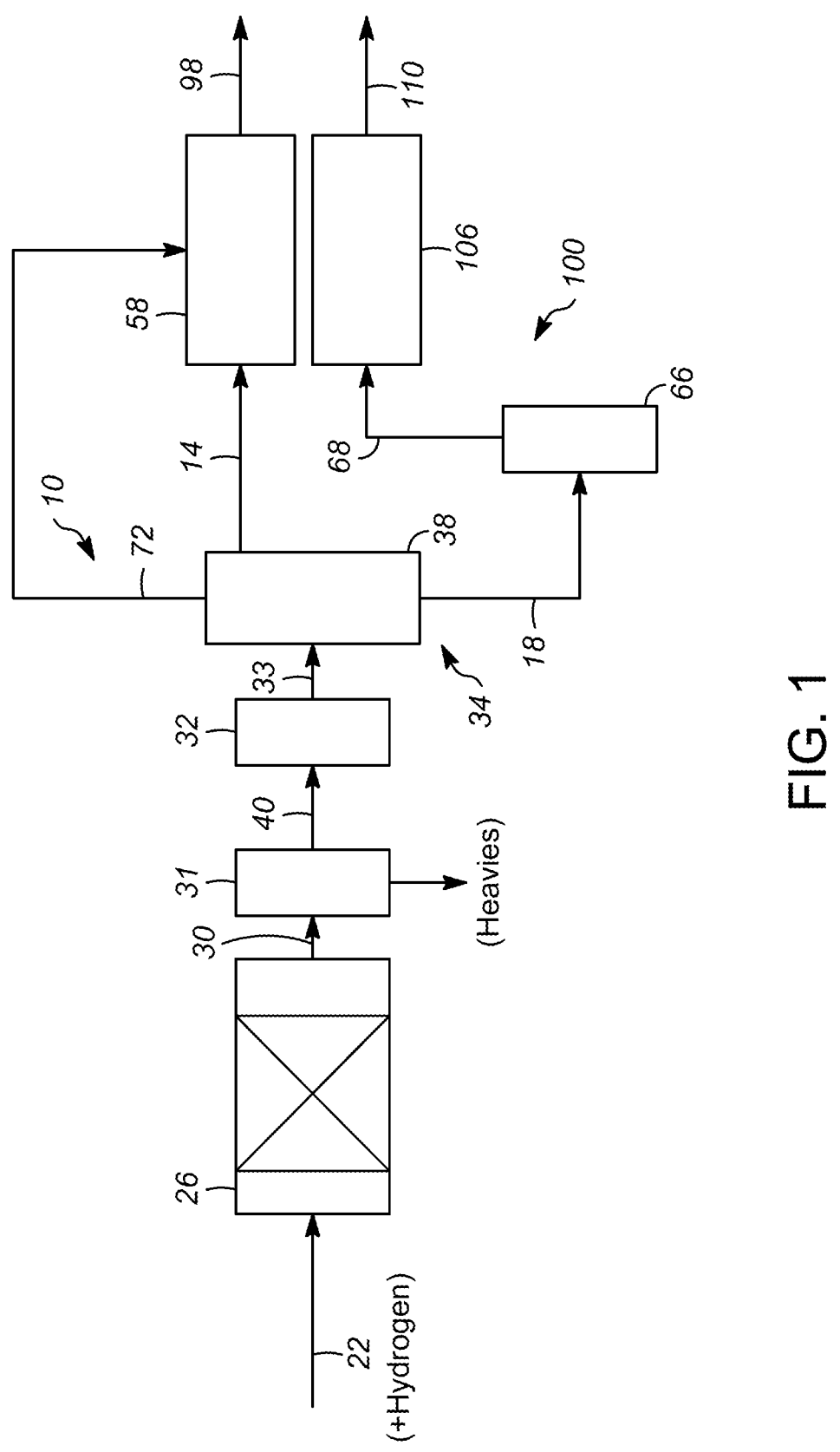
FIG. 1 is a schematic of a naphtha-to-ethane-and-propane processing unit with a separation section.

The term "downstream" means that at least a portion of fluid flowing to the subject in downstream may operatively flow from the object with which it fluidly communicates.

The term "upstream" means that at least a portion of the fluid flowing from the subject in upstream may operatively flow to the object with which it fluidly communicates.

The term "direct" means that fluid flow from the upstream component enters the downstream component without passing through any other intervening vessel.

The term "indirect" means that fluid flow from the upstream component enters the downstream component after passing through an intervening vessel.

The term "bypass" means that the object is out of downstream communication with a bypassing subject at least to the extent of bypassing.

As used herein, the term "rich" is defined as at least 50 mol %.

As mentioned above, a process and method for separating effluent from a naphtha-to-ethane-and-propane (NEP) reactor section, for which the feed is naphtha, into ethane, propane, and hydrogen/methane rich streams is described. With these general principles in mind, one or more embodiments of the present invention will be described with the understanding that the following description is not intended to be limiting.

This disclosure is directed to a process of producing light paraffins from naphtha and a stream comprising hydrogen, methane, and ethane produced in a reactor section of a naphtha-to-ethane-and-propane processing unit, including a process of separating hydrogen, methane, ethane, propane and C4 hydrocarbons in a deethanizer column configured as a dividing wall column (DWC), which is part of a fractionation section of a naphtha-to-ethane-and-propane (NEP) processing unit. The ethane and propane form feedstocks for an ethane steam cracker (ESC) and a propane de-hydrogenation unit (PDH). The propane dehydrogenation is a process in which light paraffins such as propane can be dehydrogenated to make propylene. Dehydrogenation is an endothermic reaction which requires external heat to drive the reaction to completion. This configuration is part of an overall scheme to feed ethane to the ESC and propane to the PDH, as this enhances an increased efficiency of production of ethylene and propylene (light olefins) from the naphtha than would be possible if naphtha is fed directly to a steam cracker to produce the light olefins.

The NEP processing unit is designed to preferentially produce ethane and propane from naphtha via reacting naphtha with hydrogen. An ethane rich stream is fed to an ethylene producing unit, for example an ESC and a propane rich stream is fed a PDH. This configuration produces higher quantities of olefins, namely ethylene and propylene, than what would be possible if naphtha was directly fed to a naphtha cracker to produce olefins.

An NEP system comprises a reactor section and a fractionation section. In the reactor section, naphtha is reacted with hydrogen. An NEP reactor effluent comprises of hydrogen, methane, and substantial volumes of ethane and propane, as well as C4 paraffins and other C5 to C9+ hydrocarbon components, including C5 paraffins and C6/C7/C8/C9+ aromatics.

Figure 3:
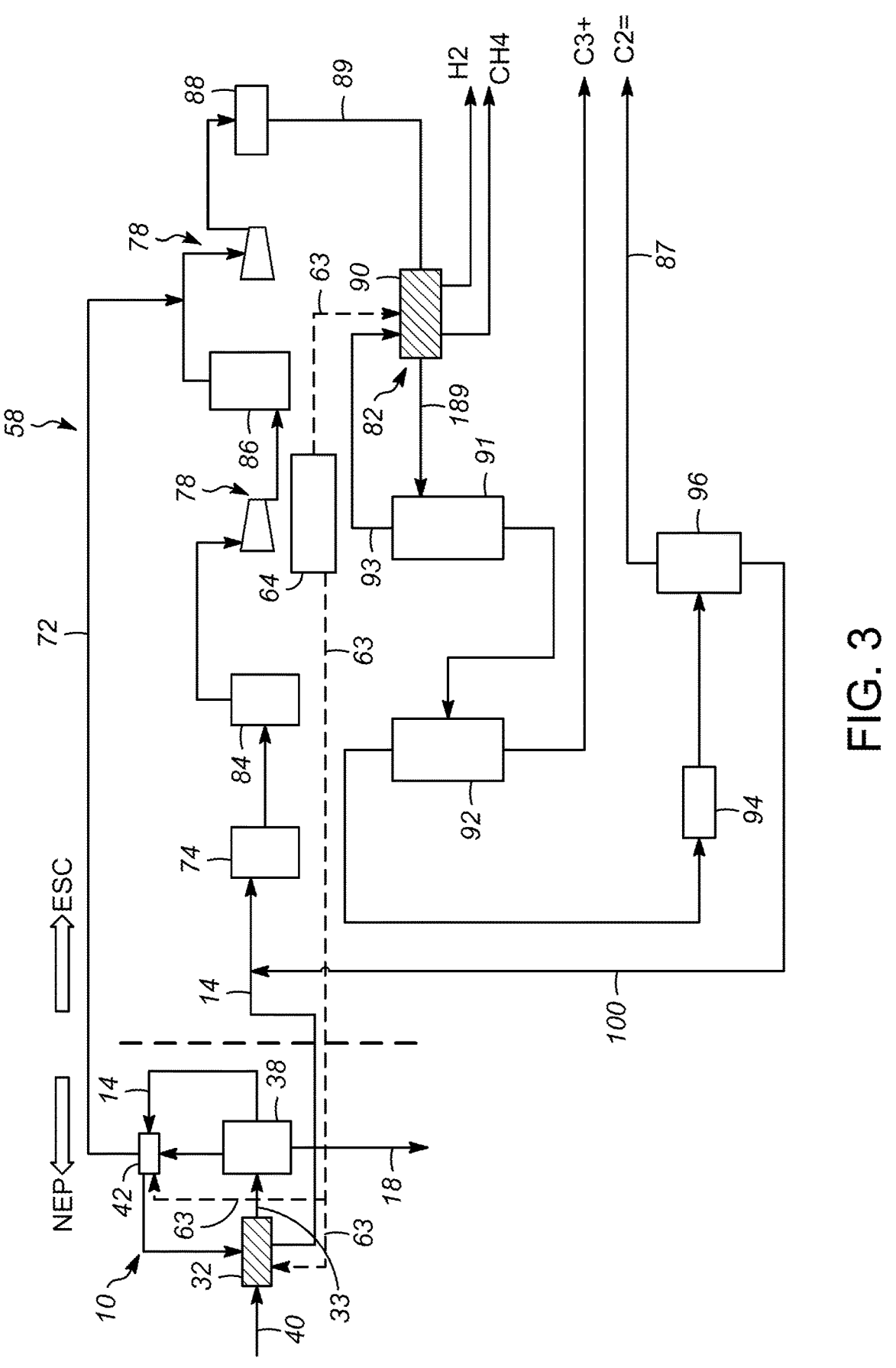
FIG. 3 is a schematic of a naphtha-to-ethane-and-propane processing unit in combination with an ethane steam cracker featuring separate coldbox heat exchangers in the naphtha-to-ethane-and-propane processing unit and the ethane steam cracker having a common source of refrigeration fluid for the coldbox heat exchangers.

The NEP fractionation section separates the reactor effluent stream into the following streams for further processing in downstream units:

a) An ethane rich stream, which is passed to the ESC to produce ethylene in cracking heaters of the ESC. The effluent stream from the ESC cracking heaters also contain hydrogen, methane, unreacted ethane, and some C3+ components. The effluent stream is cooled and quenched, caustic scrubbed, and compressed in a cracked gas compressor train. This compressed stream is subsequently fractionated in the fractionation section of the ESC using fractionating columns and refrigeration to cool the streams so that the very light boiling components can be separated. Apart from the main product, ethylene, the other product streams from the ESC include hydrogen, methane, ethane and C3+ stream. The ethane is recycled to the cracking heaters for further production of ethylene. FIG. 3 shows a schematic of an ESC. An ethane rich stream from the NEP processing unit 10 is first fed a cracking heater section of the ESC (see FIG. 3).

b) A stream comprising of hydrogen, methane, and some ethane, which is also processed in the ESC. This stream joins the ESC in the cracked gas compressor train, upstream of the cold fractionation section of the ESC. The hydrogen and methane leave the cold fractionation section while the ethane is recovered in a C2-splitter of the ESC and is recycled to the ethane cracking heaters.

c) A propane rich stream with some C4+ components is fed to a propane dehydrogenation unit (PDH) after separating the propane in a depropanizer.

The above streams a) through c) are separated in a deethanizer column of the NEP. The deethanizer column 38 is configured as a DWC. In addition to streams a) through c), the NEP fractionation section produces two other streams:

d) A C4 rich stream;

e) An aromatics byproduct stream.

The separation of these streams are relatively simple and are not part of this invention disclosure Referring to FIG. 1, generally, an NEP processing unit 10 is designed to preferentially produce an ethane rich stream 14 and a propane rich stream 18 from a naphtha stream 22 via reacting naphtha with hydrogen in a NEP reactor 26. An NEP reactor effluent stream 30 comprising a light paraffin stream is discharged from the NEP reactor 26.

The naphtha stream 22 may comprise C4 to C12 hydrocarbons preferably having a T10 between about 0-10° C. and about 60° C. and a T90 between about 70 and about 180° C. The naphtha stream 22 may comprise normal paraffins, iso-paraffins, naphthenes, and aromatics. The naphtha stream 22 may be heated to a reaction temperature of between about 300° C. and about 550° C. and preferably between about 325° C. and about 525° C.

The NEP reactor effluent 30 may comprise hydrogen, methane, ethane, propane, and residual C4+. Preferably, the NEP reactor effluent comprises at least 40 wt % ethane or at least 40 wt % propane or at least 70 wt % and preferably at least 80 wt % ethane and propane. The ethane to propane ratio can range from 0.1 to 5. The light paraffin stream can have less than about 15 wt %, suitably less than about 12 wt %, more suitably less than about 10 wt %, preferably less than about 8 wt %, more preferably less than about 6 wt % and most preferably less than about 5 wt % methane. The NEP reactor effluent 30 is passed through coolers, separators for removing the heavier ends and multiple stages of compression and shown collectively as block 31 in FIG. 1. The cooled vapor stream 40 from block 31 passes to a cooling unit, consisting of one or more multi-stream coldbox heat exchangers to produce a feed stream 33 comprising hydrogen, methane, and substantial volumes of ethane and propane, as well as a minor quantity of C4+ hydrocarbons to NEP separation section 34. The deethanizer produces an ethane rich stream (14) and a hydrogen/methane rich stream (72) both of which are routed to ESC 58. The deethanizer 38 DWC also produces a propane rich stream 18 which is sent to depropanizer 66 to produce a purified propane stream 68 and routed to a PDH 106. FIG. 1 is a simplified diagram of the flowscheme. The deethanizer configured as DWC and associated coldbox are the focus of this invention and described in more detail in the following paragraphs.

Figure 2:
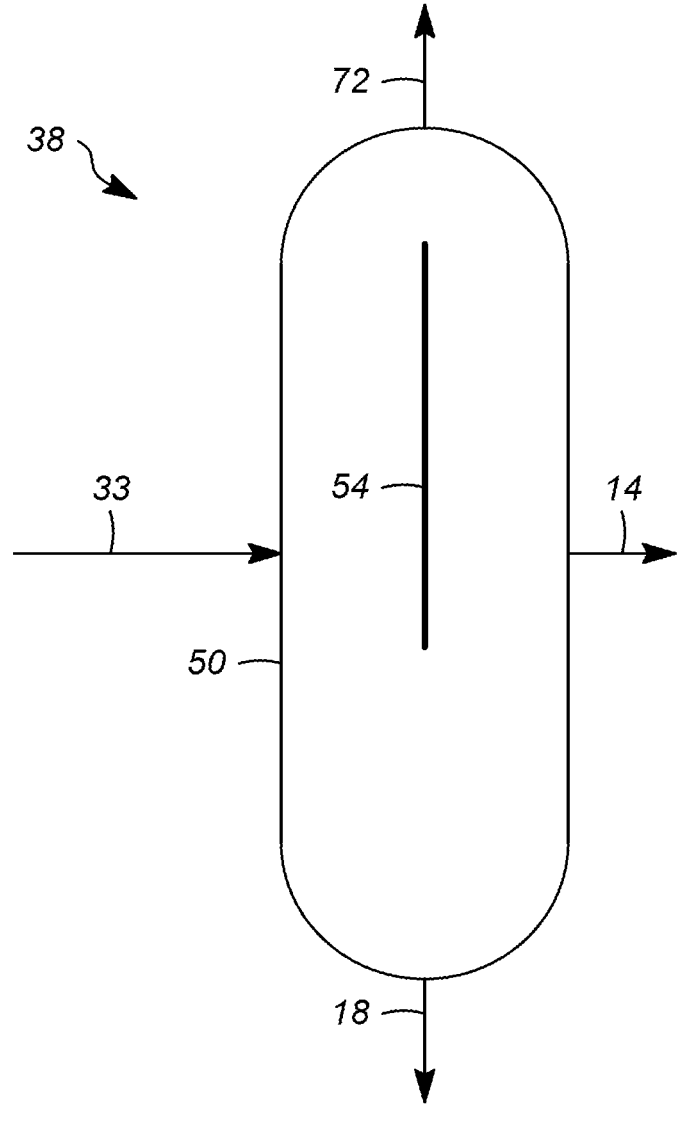
FIG. 2 is a schematic of a separation section of a divided wall fractionation column.
Figure 4:
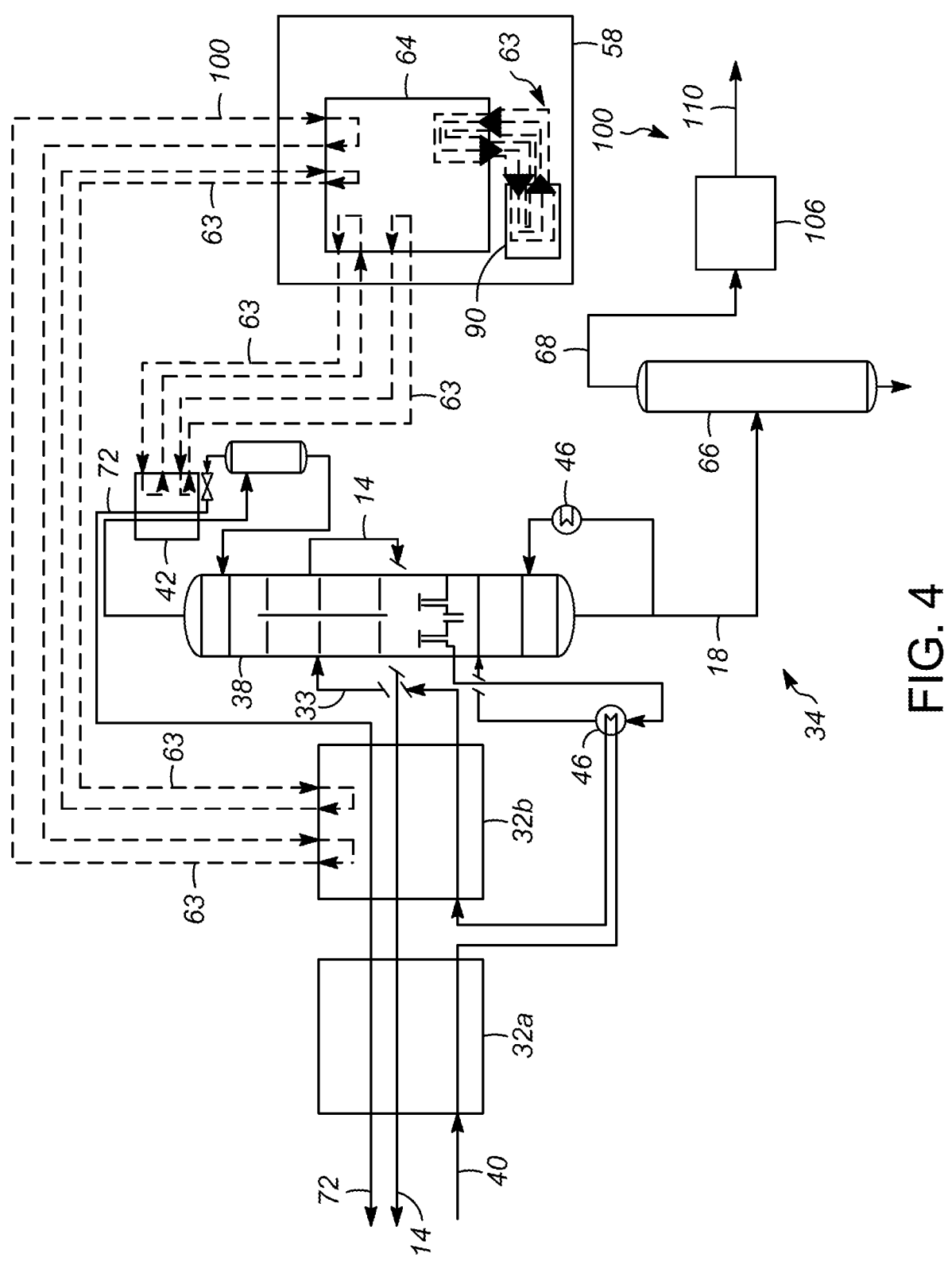
FIG. 4 is a schematic of a naphtha-to-ethane-and-propane processing unit's dividing wall column and the associated coldbox exchangers are shown in detail.

According to the present disclosure, the NEP separation section 34 comprises, among other equipment, a deethanizer 38 and a depropanizer 66 (see FIGS. 1 and 4). The deethanizer 38 is configured as a dividing wall fractionation column and its structure is depicted in FIG. 2. FIGS. 3 and 4 show the deethanizer 38 as a DWC in more detail along with its associated reboilers and condenser. While FIG. 3 shows the location of the DWC in the overall flow scheme and how it is linked to the ESC 58, FIG. 4 shows the DWC and its associated cryogenic exchangers in more detail. The deethanizer 38 DWC is a type of distillation column that can separate mixtures of several components into three or more high-purity streams. The deethanizer 38 DWC requires much less energy, capital investment, and plant space than conventional columns in series or parallel configurations. The concept of the deethanizer 38 DWC is well-established, with much literature focusing on the simulation and control. The deethanizer 38 DWC is a fully thermally coupled distillation column set-up with at least one condenser 42 and at least one reboiler 46 regardless of the number of products. The entire sequence is housed into a single shell 50 by means of one or more vertical partition walls 54 (see FIG. 2 for reference).

Thus, the deethanizer 38 DWC inputs the feed stream 33 and outputs the following streams: (1) a side product of the ethane rich stream 14, which is passed to an ethane producing unit such as the ESC 58, (2) a bottom product 18 comprising a propane rich stream, as well as other heavy products, which is passed to the depropanizer 66, and (3) a top product stream 72 comprising top product stream comprising hydrogen a methane, some slipped (residual) ethane. The coldbox 32 associated with the deethanizer 38 DWC cools the incoming stream to the deethanizer 38 DWC using the cold streams produced from the deethanizer 38 DWC (see FIGS. 3 and 4). The benefits of the feed cooling scheme are shown in Table 1. Example No. 2. The rest of the refrigeration duty of the deethanizer 38 DWC may be provided by one or more refrigeration fluid streams 63 (designated by broken/dashed lines) refrigeration streams flowing from a source of refrigeration fluid streams 64, which is shown in FIG. 3 as residing in the ESC 58; however, it should be understood that this source of refrigeration fluid streams may reside in the NEP processing unit 10 or some other locations as desired.

The ethane rich stream 14 is of relatively high purity and is a vapor side product of the deethanizer 38 DWC. Withdrawing this ethane rich vapor side product from the deethanizer 38 DWC lowers a refrigeration requirement for the deethanizer 38 DWC and reduces energy for vaporization in the ESC 58. In a preferred case, the ethane rich stream 14 is sent to the ESC 58, optionally to the ESC 58 via the coldbox 32a,b, and the vapor side product is withdrawn from the DWC eliminates energy for vaporization in the ESC 58. The ethane vapor drawn from the DWC is cold with respect to the feed stream 40 and is therefore utilized to cool the relatively warm (near ambient and approximately 40° C.) feed streams entering the coldbox exchangers in 32b and 32a (see FIG. 4) from the compression system, followed by coolers and separators. The compression system, coolers and separators are described above in the description of FIG. 1.

The ethane rich stream 14 is passed to the ESC 58. Referring to FIG. 3, generally, the ESC 58 includes a cracking heater section 74, a cracked gas compressor section 78, and a chilling section 82. The ethane rich stream 14 is passed from the deethanizer 38 DWC wherein an output stream of the ESC 58 is an ethylene rich stream 87.

The ethane rich stream 14 is initially passed to the cracking heater section 74 of the ESC 58. The ethane rich stream 14 is cracked under steam in the cracking heater section 74 to produce a cracked gas stream (cracking heater effluent) including ethylene, unreacted ethane, hydrogen, methane, and other components. The cracked stream exiting the cracking heater section 74 may be in a superheated state. One or more quench columns 84 are used for quenching or separating the cracked stream into a plurality of cracked streams. Cracking heater effluent from the quench columns 84 is then passed to compression and separation.

Compression of the cracking heater effluent is performed in the cracked gas compression section 78. Carbon dioxide and acidic sulfur compounds are removed from the cracked gas in a caustic scrubber 87. The compressed cracking heater effluent is cooled and subsequently dried in a dryer 88 by molecular sieves that remove most of the water.

The dried cracking heater effluent 89 is passed to a cooling unit such as a coldbox 90. Hydrogen and light hydrocarbons are removed from the cracked gas in the coldbox 90.

Condensates from the coldbox 90 are fed to a series of separation columns 91, 92. In a first column 91, a methane stream 93 is obtained from the top and passed to the coldbox 90, while a bottom stream is fed to a second column 92, which is a deethanizer.

A top product of the second column 92, composed primarily of ethylene and ethane, is fed to an acetylene converter 94 and then fractionated in a C2-splitter 96.

An ethylene stream 86 is withdrawn from the C2-splitter 96 as a side product. Ethane, from C2-splitter bottom product 99, is recycled to the cracking heater section 74

The top product stream 72 of the deethanizer 38 DWC comprises a stream comprising hydrogen, methane, and some slipped (residual) ethane. Thus, some ethane components are allowed to slip with the top product stream 72. The amount of ethane components allowed to slip is adjusted and controlled to optimize overhead temperature and refrigeration requirements. For example, recovering 90% of ethane feed to DWC in side product of DWC vs. 97%—recovery, results in approximately –47° C. (52° F.) overhead temperature of DWC against –71° C. (–96° F.) for the latter case. The result is deeper refrigeration for the latter case, requiring 20-25% higher refrigeration compressor power requirement for the NEP. The top product stream 72 bypasses the cracking heater section 74 and is passed to the cracked gas compressor 78 of the ESC 58. In this way, the chilling section 82 of the ESC 58 is utilized to recover and separate the hydrogen and methane. This allows additional chilling section equipment for recovery of hydrogen and methane to be eliminated from the NEP separation section 34. The slipped (residual) ethane in the top produce stream helps to keep the DWC overhead temperature higher than would be possible with minimum ethane slippage and this in turn helps to reduce refrigeration compressor power attributable to NEP requirements.

As shown in FIG. 4, the top product stream 72 may be passed to the NEP coldbox 32b prior to passing to the ESC 58.

The ethane in the top product stream 72 that bypasses the cracking heater section 74 is recovered in an ESC C2-splitter 96 downstream from the cracked gas compressor 78, the ESC coldbox 90, and ESC columns 91 (demethanizer), 92 (deethanizer). Ethane slippage with the DWC top product stream 72 is optimized in conjunction with energy required for separation of additional ethane in the ESC C2-splitter 96. It is contemplated that the ethane slippage can be varied between 5% to 20% of the net ethane produced in the NEP processing unit 10.

The net bottom product 18 withdrawn from the deethanizer 38 DWC comprises a stream comprising propane and C4s as well as other heavy products. As shown in FIG. 4, the bottom product 18 is passed to a depropanizer column 66. A propane rich stream 68 is fed to propane dehydrogenation unit (PDH) 106. A propane rich stream 68 is withdrawn from the depropanizer 66 and sent to the PDH 106, where the desired propylene product 110 is output.

According to the present disclosure, the ethane rich stream 14 passed to the ESC 58 and the propane stream 18 passed to the PDH 106 produce higher quantities of olefins (ethylene and propylene) due to the DWC (since it helps to produce ethane and propane rich streams by effective separation), than what would be possible if naphtha was directly fed to a naphtha cracker to produce olefins. The other novelties and advantages of the proposed scheme are elaborated in the subsequent sections.

However, the products of the NEP reactor 26 contain light products, e.g., hydrogen and methane, along with ethane and propane. As shown in FIG. 1, and as discussed in the preceding sections, the NEP processing unit 10 with incorporation of a DWC type deethanizer 38 and using shared refrigeration equipment with an ESC (see FIGS. 3-5) is a cost-efficient method of separating H2 and CH4 from ethane and propane produced in NEP reactor 26. Careful separation of streams produced in the NEP reactor section 26 together with using the coldbox 90 of the ESC 58 to separate H2 from CH4 which were produced in the NEP processing unit 10, makes this scheme of using shared assets between NEP processing unit 10 and the ESC 58 optimal regarding both operating and capital expenses.

Advantages of employing the deethanizer 38 DWC in this process include a reduction in overall energy usage. The DWC system is 15% more efficient than traditional two-column systems. Also, the DWC system reduces the equipment count compared to alternative flow scheme using membrane systems. Utilizing the deethanizer 38 DWC is an innovative way to achieve the separation of 3 streams of desired purity: (1) hydrogen/H4 rich gas as a top product stream 72; (2) an ethane rich 14 stream as a side product; and (3) a propane rich stream 18 as the bottom product 18 in a single column.

It is further contemplated that the principles of this disclosure result in greater carbon efficiency (>70%) that prior processes (45%-55%). Corresponding lower by-product yields and 40%-70% lower fuel gas make the process disclosed herein hydrogen self-sufficient. Finally, the process of this disclosure improves flexibility at design stage for high P:E (ratio of propylene to ethylene) to low P:E with catalyst and processing condition change in NEP reactor section.

Further according to this disclosure, C2 components are allowed to slip with the top product stream 72. The amount or volume of C2 allowed to slip is controlled. This allows optimization of the overhead temperature and refrigeration requirements and thus helps to reduce the overall energy usage.

The hydrogen and methane rich stream is passed to the cracked gas compressor section 78 and further on to the ESC cooling/separation section, bypassing the cracking heater section 74 since these components are not desired feed for the cracking heaters of the ESC 58. In this way the ESC cooling unit (coldbox 90, is utilized to recover the H2 and the CH4). Thus, the need for additional cooling units for recovery and separation of H2 and CH4 is eliminated in the NEP separation section 34.

The C2s in the hydrogen rich stream which bypass the ESC cracking heater section 74 are recovered in the ESC C2-splitter 96. Optimizing the C2 slippage with deethanizer 38 DWC top product stream 72 stream optimizes energy required for separation in the ESC 58 C2-splitter 96. The C2 slippage can be varied between 5% to 20% of the net C2s produced in the NEP processing unit 10.

The disclosed process is approximately 15% more energy efficient when compared to a traditional two column process system.

The DWC helps to eliminate hydrogen and CH4 entering the ESC cracking heater section 74 with feed ethane. This is not possible in other alternative systems. Approximately 10%-15% volumetric flow reduction through the ESC heaters result with consequent benefits in capex of heaters and associated equipment. This also results in separation of components which do not result in ethylene production in cracking heaters in ESC.

According to the present disclosure, cold streams and the deethanizer 38 DWC side reboiler 46 may be used for heat recovery. There is additional heat recovery from the cold ethane rich stream 14 and hydrogen stream 72 coming out of the deethanizer 38 DWC. The balance of the cooling may be derived from the refrigeration system which may be common for the ESC 58 and NEP 10 and shown as 64. Cooling may be shared between the ESC 58 and the NEP processing unit 10. A refrigeration system including compressors can be located in the ESC 58 and are shown as 64, and the NEP coldbox 32 can derive the refrigerant fluid flow as required. NEP coldbox 32 refrigeration requirement is approximately 25% of the ESC coldbox 90 requirement.

The system is flexible towards the refrigeration system selected for the ESC 58 and both mixed refrigeration system (MR) or cascade (ethylene-propylene) refrigeration system can be used.

This disclosure is further directed to integration of the NEP processing unit 10 comprising the deethanizer 38 DWC with the ESC 58. The integration disclosed herein achieves a passing of the ethane rich stream 14 produced in the NEP processing unit 10 to the cracking heater section 74 of the ESC 58. The integration further achieves passing the top product stream 72 of hydrogen, methane, and ethane slip from the deethanizer 38 DWC top to the cracked gas compressor section 78 of the ESC 58. The hydrogen and the methane are separated in the coldbox 90 of the ESC 58 while the ethane rich stream is eventually separated in the C2-splitter bottom product 99 and passed to the ethane cracking heater section 74 of the ESC 58. The ethane content in this stream is about 5% to 20% of the total ethane produced in the NEP reactor 26, which is passed to the deethanizer 38 DWC as feed. The NEP processing unit 10 and the ESC 58 can use shared refrigeration equipment.

According to the present disclosure, the NEP processing unit 10 and the ESC 58 can share a common refrigeration system with a common source of refrigeration fluid(s) 64. One or more refrigeration fluids 63 are passed from the common source of refrigeration fluid(s) 64 to a coldbox 32 of the NEP processing unit 10 and to a coldbox 90 of the ESC 58. FIG. 4 shows 2 levels of cascade propylene-ethylene refrigeration (propylene refrigerant may be of approximately $-4°$ C. and drawn $3^{rd}$ stage suction and of approximately $-16°$ C. and drawn from $2^{nd}$ stage suction) for NEP coldbox 32b while the DWC condenser 42 shows 1 level of ethylene refrigeration (may be of approximately $-45°$ C. drawn from $3^{rd}$ stage suction) and 1 level of propylene (may be approximately $-37°$ C. and drawn from first stage). The ESC coldbox 90 has multiple levels of cascade ethylene-propylene refrigeration but not shown, for simplicity and since this coldbox 90 is not the focus of the present disclosure. The focus and the illustrations are intended to show that NEP refrigeration requirements can make use of available and appropriate refrigeration streams available for the ESC coldbox 90, which is the main user of the refrigeration streams, as explained above. Hence, it is emphasized that the cascade refrigeration system of ethylene-propylene and the temperature levels indicated above can vary by approximately $±5°$ C., and the design of the NEP coldbox 32a,b and the DWC condenser 42 can be configured to make use of the available levels of refrigeration. The cascade ethylene-propylene refrigeration system could also be replaced by single mixed refrigeration system for both NEP and ESC.

Figure 5:
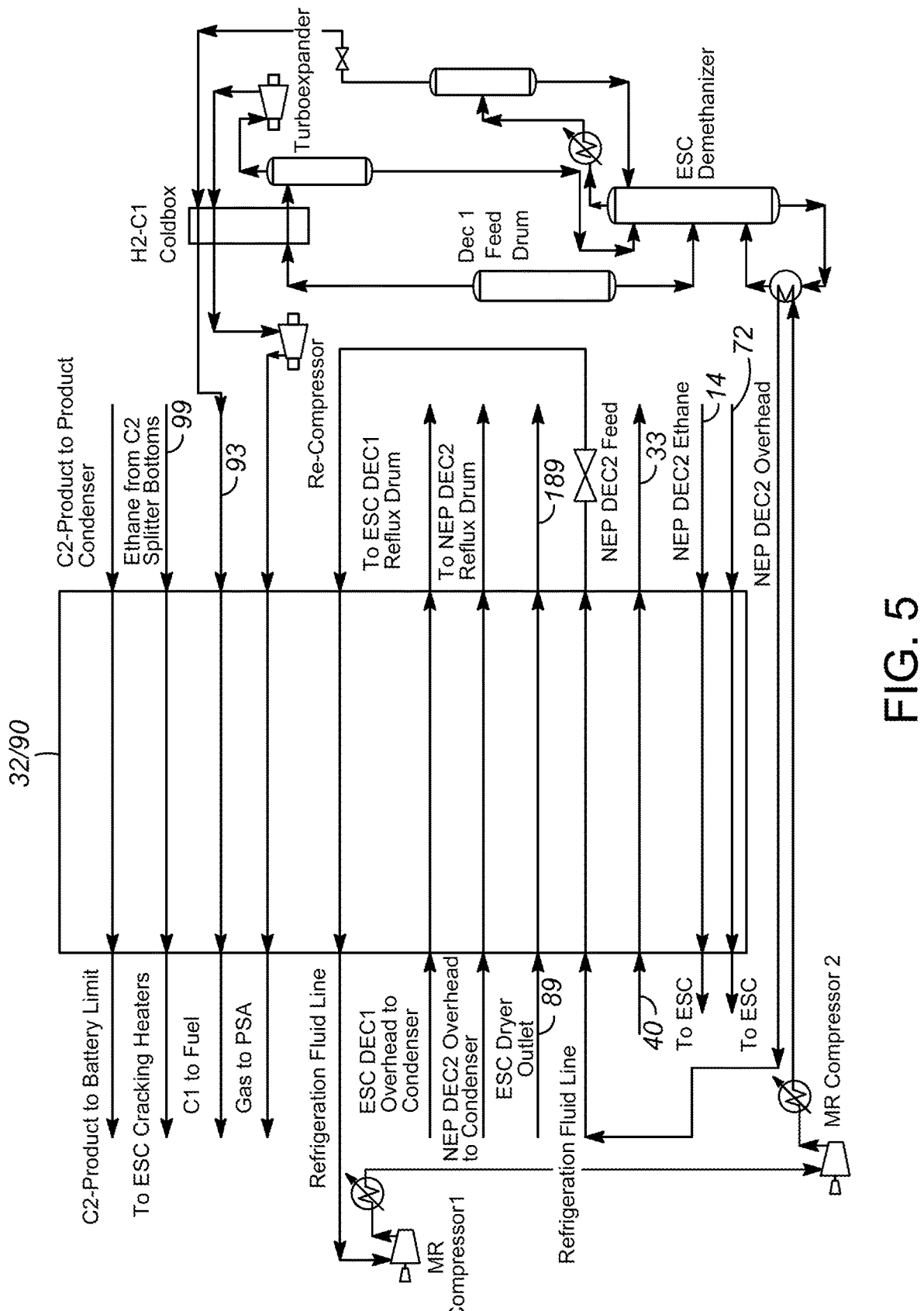
FIG. 5 is a schematic of a common coldbox and a mixed refrigeration system (MR) provided to integrate a naphtha-to-ethane-and-propane processing unit with an ethane steam cracker.

Alternatively, referring to FIG. 5, it is contemplated that the NEP processing unit 10 and the ESC 58 can share a common coldbox 32/90 and a common mixed refrigeration system (MR). This cold box will process all the cold streams of the NEP processing unit 10 and the ESC 58 and use these streams to cool the incoming warm streams that need to be cooled. Here, on the NEP processing unit 10 side of the common coldbox 32/90, the NEP reactor section effluent stream 40 passes through the common coldbox 32/90 to become the cooled feed stream 33 to the deethanizer 38 DWC; the top net vapor product stream 72 passes through the common coldbox 32/90 and is warmed prior to passing to the ESC 58; the ethane rich stream 14 passed from the deethanizer 38 DWC passes through the common coldbox 32/90 and is warmed prior to passing to the ESC 58; the NEP DWC overhead stream (not numbered) is cooled and condensed before entering the NEP DWC reflux drum (not numbered). The ESC 58 side of the common coldbox 32/90 receives the dried cracking heater effluent stream 89 from the dryer 88 and is cooled to stream 189 to be fed to ESC demethanizer 91; the methane stream 93 from top of the first column (demethanizer) 91 enters the common coldbox 32/90 and is warmed and sent to fuel gas. There are many other streams originating in the ESC 58, such as cold hydrogen rich gas originating in the ESC 58 and sent as warmed hydrogen rich gas, possibly to PSA; an ESC demethanizer overhead stream is condensed and is sent to a demethanizer condenser; an ethane rich stream from the ESC C2 splitter 96 bottoms and is warmed and sent to ESC Cracking heaters 74; liquid ethylene product is vaporized in coldbox 32/90 and sent to a desired destination. The unbalanced refrigeration requirement can be met by mixed refrigeration system. The intent is to design an integrated common coldbox 32/90 for both NEP processing unit 10 and the ESC 58 and have a common mixed refrigeration system also.

While the specific embodiments have been illustrated and described, numerous modifications come to mind without significantly departing from the spirit of the invention, and the scope of protection is only limited by the scope of the accompanying Claims.

TABLE 1

| OPEX BENEFITS OF DWC SCHEME IN NEP FRACTIONATION SECTION | | | |
|---|---|---|---|
| Example No. | Item Description | Benefits | Remarks on Benefits |
| 1 | Energy benefit - DWC relative to conventional two column system | 0.85 base | Base = Energy usage with a two column system |
| 2 | Energy benefit - with heat integration in NEP cold box relative to no heat integration | 30% reduction for DWC feed cooling duty 5% reduction for DWC condenser duty | |
| 3 | Energy benefits: (Overhead condenser duty reduction) for vapor side draw relative to liquid side draw in DWC | 0.4 to 0.45 of Base | Base = Condenser duty with a liquid side draw. All other column operation parameters (Vapor side draw vs liquid side draw) being comparable |
| 4 | Reduction in volumetric flow to Ethane Cracking Heaters due to separation of H2 and methane in DWC overhead | 15% reduction | Approximately 15% reduction in volumetric flow to ethane cracking heaters due to separation of H2/methane in DWC overhead H2/Methane do not crack to result in ethylene make in ethane crackers |
| 5 | Energy benefit: higher DWC overhead temperature with Ethane slip relative to without Ethane slip and consequent reduced refrigeration duty | 0.75 of base to 0.85 of base @ 90% C2 recovery in DWC side product compared to 97% C2 recovery (considered as base) | C2 slip in overhead allows higher DWC overhead temperature -- which in turn means lower power usage of refrigeration compressors. 90% C2 recovery results in −47° C./−52° F. overhead temperature where as 97% C2 recovery (implying purer H2/CH4 in DWC overhead) results in −71° C./−96° F. DWC overhead temperature -- all other parameters being comparable. The higher DWC overhead temperature results in reduced refrigeration compression power (75% to 80% of BASE; where BASE = NEP refrigeration compressor power at 97% C2 recovery as DWC side product C2 slippage (residual) in DWC overhead can be looked in conjunction with additional separation needs in ESC C2 Splitter |

TABLE 2

CAPEX BENEFITS DUE TO INTEGRATION
BETWEEN NEP AND ESC

| Example No. | Configuration | Benefits |
|---|---|---|
| 1 | Separate cold boxes for NEP and ESC but using common refrigeration system | Eliminates need for separate refrigeration system (refrigeration compressor with drivers, suction drum, some exchangers Reduce CAPEX of NEP Reduce plot area Easy to design and execute Refrigeration needs will be primarily governed by ESC, and NEP will be supplied with refrigeration streams |
| 2 | Use ESC cold box to separate H2 and Methane generated in NEP | Avoids need for deep refrigeration and system to separate hydrogen from methane in NEP fractionation section Eliminates need for independent H2/methane separation system within NEP (reduced cold box exchangers, deep refrigeration equipment) Reduced CAPEX for NEP by synergizing separation requirement of NEP and ESC |

Specific Embodiments

While the following is described in conjunction with specific embodiments, it will be understood that this description is intended to illustrate and not limit the scope of the preceding description and the appended claims.

A first embodiment of the invention is a process of producing ethylene and propylene from naphtha, the process comprising passing a feed stream comprising hydrogen, methane, ethane, and propane and residual C4+ from a naphtha-to-ethane-and-propane reactor to a dividing wall fractionation column. An embodiment of the invention is one, any or all of prior embodiments in this paragraph up through the first embodiment in this paragraph wherein a top product stream outputted by the dividing wall fractionation column, the top product stream comprising hydrogen, methane, and some slipped ethane (residual), a side product comprises an ethane rich stream, and a bottom product stream comprises propane and other heavy products. An embodiment of the invention is one, any or all of prior embodiments in this paragraph up through the first embodiment in this paragraph further comprising controlling an overhead temperature of the dividing wall column and refrigeration energy requirements by controlling an amount of the slipped ethane allowed in the top stream product of the dividing wall column. An embodiment of the invention is one, any or all of prior embodiments in this paragraph up through the first embodiment in this paragraph further comprising passing the top product stream to a cracked gas compressor system of an ethane steam cracker, bypassing a cracking heater section of the ethane steam cracker. An embodiment of the invention is one, any or all of prior embodiments in this paragraph up through the first embodiment in this paragraph further comprising passing the ethane rich stream from the dividing wall fractionation column to an ethane steam cracker after heat exchange in a plurality of coldbox exchangers with a warm feed stream and thereby reducing a refrigeration requirement for feed cooling. An embodiment of the invention is one, any or all of prior embodiments in this paragraph up through the first embodiment in this paragraph further comprising passing the ethane rich stream to a cracking heater section of the ethane steam cracker, wherein an ethylene stream is output from the ethane steam cracker. An embodiment of the invention is one, any or all of prior embodiments in this paragraph up through the first embodiment in this paragraph wherein the stream the ethane rich stream is a vapor side product of the dividing wall fractionation column, and wherein withdrawing the ethane rich stream as a vapor side product from the dividing wall fractionation column lowers a refrigeration requirement for the dividing wall fractionation column and reduces energy for vaporization in the ethane steam cracker. An embodiment of the invention is one, any or all of prior embodiments in this paragraph up through the first embodiment in this paragraph wherein the energy for vaporization in the ethane rich steam cracker is eliminated by the vapor side product and wherein a further energy reduction takes place by utilizing the ethane rich stream and the top product to cool fluids passing through the plurality of coldbox exchangers. An embodiment of the invention is one, any or all of prior embodiments in this paragraph up through the first embodiment in this paragraph further comprising passing the propane rich stream from the dividing wall fractionation column to a propane dehydrogenation unit after further fractionation in a depropanizer column. An embodiment of the invention is one, any or all of prior embodiments in this paragraph up through the first embodiment in this paragraph further comprising passing a top product stream outputted by the dividing wall fractionation column to a cracked gas compressor of an ethane steam cracker; passing an ethane rich stream outputted by the dividing wall fractionation column to the ethane stream cracker, wherein an ethylene stream is output from the ethane steam cracker; and passing a propane rich stream outputted by the dividing wall fractionation column and after fractionation in a depropanizer to a propane dehydrogenation unit, wherein a propylene stream is output from the propane dehydrogenation unit, wherein the top product stream bypasses a cracking heater section of the ethane steam cracker, and thereby reducing a feed flow to the cracking heater section of hydrogen and methane which do not contribute to production of ethylene in the cracking heaters, and wherein a chilling section and cold fractionation section of the ethane steam cracker is configured to recover hydrogen and methane as well as ethane in a C2 splitter. An embodiment of the invention is one, any or all of prior embodiments in this paragraph up through the first embodiment in this paragraph further comprising passing the feed stream through at least one coldbox prior to passing the feed stream to the dividing wall fractionation column and thereby reducing a refrigeration requirement for cooling the feed stream to the dividing wall fractionation column.

A second embodiment of the invention is an apparatus for producing ethylene and propylene from naphtha comprising an effluent from a naphtha-to-ethane-and-propane processing unit which separates an ethane rich stream and a propane rich stream from a stream comprising ethane, propane, hydrogen, methane, and residual C4+ heavy hydrocarbons, the naphtha-to-ethane-and-propane processing unit comprising a dividing wall fractionation column which receives the effluent stream from an naphtha-to-ethane-and-propane reactor and outputs a top product stream comprising hydrogen and methane, the ethane rich stream as a side product, and the propane rich stream comprising residual C4+ hydrocarbons as a bottom product. An embodiment of the invention is one, any or all of prior embodiments in this paragraph up through the second embodiment in this paragraph further comprising an ethane steam cracker configured to input the ethane rich stream from the dividing wall fractionation column and output a stream of ethylene. An embodiment of the invention is one, any or all of prior embodiments in this paragraph up through the second embodiment in this paragraph wherein the ethane rich stream is a vapor side product of the dividing wall fractionation column. An embodiment of the invention is one, any or all of prior embodiments in this paragraph up through the second embodiment in this paragraph wherein withdrawing the ethane rich stream as a vapor side product from the divided wall fractionation column lowers a refrigeration requirement for the divided wall fractionation column and reduces energy for vaporization in the ethane steam cracker. An embodiment of the invention is one, any or all of prior embodiments in this paragraph up through the second embodiment in this paragraph further comprising a depropanizer column configured to input the propane rich stream from the divided wall fractionation column. An embodiment of the invention is one, any or all of prior embodiments in this paragraph up through the second embodiment in this paragraph further comprising a propane dehydrogenation unit configured to input an output product from the depropanizer column and output a stream of propylene. An embodiment of the invention is one, any or all of prior embodiments in this paragraph up through the second embodiment in this paragraph wherein the top product stream output from the dividing wall fractionation column bypasses a cracking heater section of the ethylene steam cracker. An embodiment of the invention is one, any or all of prior embodiments in this paragraph up through the second embodiment in this paragraph wherein the naphtha-to-ethane-and-propane processing unit further comprises a coldbox wherein the effluent passes through the coldbox upstream of the dividing wall fractionation column exchanging heat with incoming feed to dividing wall column. 20

A third embodiment of the invention is a process of producing ethylene and propylene from naphtha, the process comprising passing a feed stream comprising hydrogen, methane, ethane, and propane and residual C4+ from a naphtha-to-ethane-and-propane reactor through a coldbox; passing the feed stream from the coldbox to a dividing wall fractionation column passing a top product stream from the dividing wall fractionation column, the top product stream comprising hydrogen, methane, and some slipped ethane (residual); passing the top product stream to a cracked gas compressor system of an ethane steam cracker and bypassing a cracking heater section of the ethane steam cracker; passing a side product comprising an ethane rich stream from dividing wall fractionation column; passing the ethane rich stream from the dividing wall fractionation column to a cracking heater section of the ethane steam cracker; passing an ethylene stream from the ethane steam cracker; passing a bottom product stream comprising propane and other heavy products from the dividing wall fractionation column; passing the propane rich stream from the dividing wall fractionation column to a propane dehydrogenation unit after further fractionation in a depropanizer column; and passing a propylene stream is from the propane dehydrogenation unit, wherein the ethane rich stream is a vapor side product of the dividing wall fractionation column, wherein withdrawing the ethane rich stream as a vapor side product from the dividing wall fractionation column lowers a refrigeration requirement for the dividing wall fractionation column and reduces an energy for vaporization in the ethane steam cracker, and wherein the energy for vaporization in the ethane rich steam cracker is eliminated by the vapor side product and wherein a further energy reduction takes place by utilizing the ethane rich stream and the top product stream to cool fluids passing through the coldbox.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process of producing ethylene and propylene from naphtha, the process comprising:

passing a feed stream comprising hydrogen, methane, ethane, and propane and residual C4+ from a naphtha-to-ethane-and-propane reactor to a dividing wall fractionation column, wherein a top product stream is outputted by the dividing wall fractionation column, the top product stream comprising hydrogen, methane, and some slipped ethane (residual), a side product comprises an ethane rich stream, and a bottom product stream comprises propane and other heavy products, and passing a top product stream to a cracked gas compressor system of an ethane steam cracker, bypassing a cracking heater section of the ethane steam cracker.

2. The process of claim 1 further comprising controlling an overhead temperature of the dividing wall column and refrigeration energy requirements by controlling an amount of the slipped ethane allowed in the top stream product of the dividing wall column.

3. The process of claim 1 further comprising passing the ethane rich stream from the dividing wall fractionation column to an ethane steam cracker after heat exchange in a plurality of coldbox exchangers with a warm feed stream and thereby reducing a refrigeration requirement for feed cooling.

4. The process of claim 3 further comprising passing the ethane rich stream to a cracking heater section of the ethane steam cracker, wherein an ethylene stream is output from the ethane steam cracker.

5. The process of claim 4 wherein the ethane rich stream is a vapor side product of the dividing wall fractionation column, and wherein withdrawing the ethane rich stream as a vapor side product from the dividing wall fractionation column lowers a refrigeration requirement for the dividing wall fractionation column and reduces energy for vaporization in the ethane steam cracker.

6. The process of claim 5 wherein the energy for vaporization in the ethane rich steam cracker is eliminated by the vapor side product and wherein a further energy reduction takes place by utilizing the ethane rich stream and the top product to cool fluids passing through the plurality of coldbox exchangers.

7. The process of claim 1 further comprising passing the propane rich stream from the dividing wall fractionation column to a propane dehydrogenation unit after further fractionation in a depropanizer column.

8. The process of claim 1 further comprising:

passing the top product stream outputted by the dividing wall fractionation column to a cracked gas compressor of an ethane steam cracker;

passing the ethane rich stream outputted by the dividing wall fractionation column to the ethane stream cracker, wherein an ethylene stream is output from the ethane steam cracker; and passing the propane rich stream outputted by the dividing wall fractionation column and after fractionation in a depropanizer to a propane dehydrogenation unit, wherein a propylene stream is output from the propane dehydrogenation unit, wherein the top product stream bypasses a cracking heater section of the ethane steam cracker, and thereby reducing a feed flow to the cracking heater section of hydrogen and methane which do not contribute to production of ethylene in the cracking heaters, and wherein a chilling section and cold fractionation section of the ethane steam cracker is configured to recover hydrogen and methane as well as ethane in a C2 splitter.

9. The process of claim 1 further comprising passing the feed stream through at least one coldbox prior to passing the feed stream to the dividing wall fractionation column and thereby reducing a refrigeration requirement for cooling the feed stream to the dividing wall fractionation column.

10. An apparatus for producing ethylene and propylene from naphtha comprising:

an effluent from a naphtha-to-ethane-and-propane processing unit which separates an ethane rich stream and a propane rich stream from a stream comprising ethane, propane, hydrogen, methane, and residual C4+ heavy hydrocarbons, the naphtha-to-ethane-and-propane processing unit comprising:

a dividing wall fractionation column which receives the effluent stream from an naphtha-to-ethane-and-propane reactor and outputs a top product stream comprising hydrogen and methane, the ethane rich stream as a side product, and the propane rich stream comprising residual C4+ hydrocarbons as a bottom product, an ethane steam cracker configured to input the ethane rich stream from the dividing wall fractionation column and output a stream of ethylene, wherein the ethane rich stream is a vapor side product of the dividing wall fractionation column, wherein withdrawing the ethane rich stream as a vapor side product from the divided wall fractionation column lowers a refrigeration requirement for the divided wall fractionation column and reduces energy for vaporization in the ethane steam cracker, the apparatus further comprising:

a depropanizer column configured to input the propane rich stream from the divided wall fractionation column, and a propane dehydrogenation unit configured to input an output product from the depropanizer column and output a stream of propylene.

11. The apparatus of claim 10 wherein the top product stream output from the dividing wall fractionation column bypasses a cracking heater section of the ethylene steam cracker.

12. A process of producing ethylene and propylene from naphtha, the process comprising:

passing a feed stream comprising hydrogen, methane, ethane, and propane and residual C4+ from a naphtha-to-ethane-and-propane reactor to a dividing wall fractionation column, wherein the naphtha-to-ethane-and-propane processing unit further comprises a coldbox wherein the effluent passes through the coldbox upstream of the dividing wall fractionation column exchanging heat with incoming feed to dividing wall column.

\* \* \* \* \*